United States Patent [19]
Lal et al.

[11] Patent Number: 6,015,702
[45] Date of Patent: *Jan. 18, 2000

[54] HUMAN UBIQUITIN-CONJUGATING ENZYMES

[75] Inventors: Preeti Lal, Santa Clara; Jennifer L. Hillman; Neil C. Corley, both of Mountain View, all of Calif.

[73] Assignee: Incyte Pharmaceuticals, Inc., Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/965,689

[22] Filed: Nov. 6, 1997

Related U.S. Application Data

[63] Continuation-in-part of application No. 08/933,750, Sep. 23, 1997.

[51] Int. Cl.[7] .............................. C12N 9/10; C12N 1/20; C12N 15/00; C07H 21/04
[52] U.S. Cl. ................... 435/193; 435/252.3; 435/320.1; 536/23.2
[58] Field of Search ................................ 435/193, 252.3, 435/320.1; 536/23.2

[56] References Cited

PUBLICATIONS

Verma, R. et al., "Phosphorylation of Sic1p by $G_1$ Cdk Required for Its Degradation and Entry into S Phase" *Science* (1997) 278:455–460.

Ciechanover, Aaron, "The Ubiquitin–Proteasome Proteolytic Pathway" *Cell* (1994) 79:13–21.

Jentsch, Stefan, "The Ubiquitin–Conjugating System," *Annu. Rev. Genet.* (1992) 26:179–207.

Monia, B.P. et al., "Gene Synthesis, Expression, and Processing of Human Ubiquitin Carboxyl Extension Proteins." *J.Biol.Chem.* (1989) 264:4093–4103.

van Nocker, S. et al., "The Arabidopsis Thaliana UBC7/13/14 Genes Encode a Family of Multiubiquitin Chain–forming E2 Enzymes." *J.Biol.Chem.* (1996) 271:12150–12158.

Llovera, M. et al., "Muscle Wasting Associated With Cancer Cachexia is Linked to an Important Activation of the ATP–Dependent Ubiquitin–Mediated Proteolysis" *Int.J.Cancer* (1995) 61:138–141.

Gregori, L. et al., "Ubiquitin–Mediated Degradative Pathway Degrades the Extracellular but not the Intracellular form of Amyloid β–Protein Precursor" *Biochem.Biophys.Res.Commun.* (1994) 203:1731–1738.

Grant, E.P. et al., "Rate of Antigen Degradation by the Ubiquitin–Proteasome Pathway Influences MHC Class I Presentation" *J.Immunol.* (155:3750–3758).

Kershaw, J., GI 1628097, GenBank Sequence Database (Accession U39318), National Center for Biotechnology Information, National Library of Medicine, Bethesda, Maryland, 20894.

Kershaw, J., GI 1628091, GenBank Sequence Database (Accession U39318), National Center for Biotechnology Information, National Library of Medicine, Bethesda, Maryland, 20894.

Faye, G.R., GI 4257, GenBank Sequence Database (Accession U39318), National Center for Biotechnology Information, National Library of Medicine, Bethesda, Maryland, 20894.

Faye, G.R., GI 4256, GenBank Sequence Database (Accession U39318), National Center for Biotechnology Information, National Library of Medicine, Bethesda, Maryland, 20894.

*Primary Examiner*—Charles L. Patterson, Jr.
*Assistant Examiner*—Elizabeth Slobodyansky
*Attorney, Agent, or Firm*—Incyte Pharmaceuticals, Inc.; Lynn E. Murry

[57] ABSTRACT

The invention provides a human ubiquitin-conjugating enzyme (HUBI) and polynucleotides which identify and encode HUBI. The invention also provides expression vectors, host cells, agonists, antibodies and antagonists. The invention also provides methods for diagnosing, treating or preventing disorders associated with expression of HUBI.

9 Claims, 10 Drawing Sheets

```
5' NNC GCC GGG AGC CGG TGC GGC TGT GAG GGG CCG CGT CTC GCA GCA GCC
                9              18              27              36              45              54

CGG ACC GGG CAT GGT GTT GGG CGC GCC CTC GCC TGT CTC GGG GAG CCC
                63              72              81              90              99             108

AGG GTA AAG GCA GCA ATG CTA ACG CTA GCA AGT AAA CTG AAG CGT GAC GAT
                               117             126             135             144             153             162
                            M   L   T   L   A   S   K   L   K   R   D   D

GGT CTC AAA GGG TCC CGG ACG GCA GCC ACA GCG TCC GAC TCG ACT CGG AGG GTT
               171             180             189             198             207             216
    G   L   K   G   S   R   T   A   A   T   A   S   D   S   T   R   R   V

TCT GTG AGA GAC AAA GAG TTT CTT GTT AAA GAG GTT GCA GAA CTT GAA GCT AAT TTA
               225             234             243             252             261             270
    S   V   R   D   K   E   F   L   V   K   E   V   A   E   L   E   A   N   L

CCT TGT ACA TGT AAA GTG CAT TTT CCT GAT CCA AAC AAG CTT CAT TGT TTT CAG
               279             288             297             306             315             324
    P   C   T   C   K   V   H   F   P   D   P   N   K   L   H   C   F   Q
```

FIGURE 1A

```
                          333  342       351       360       369       378
CTA ACA GTA ACC CCA GAT GAG GGT TAC TAC CAG GGA AAA TTT CAG TTT GAA
 L   T   V   T   P   D   E   G   Y   Y   Q   G   K   F   Q   F   E 387  396       405       414       423       432
ACT GAA GTT CCC GAT GCG TAC AAC ATG GTG CCT CCC AAA GTG TGC CTG ACC
 T   E   V   P   D   A   Y   N   M   V   P   P   K   V   C   L   T 441  450       459       468       477       486
AAG ATC TGG CAC CCC TCA ATT ACA GAG ACA GGG GAA ATA TGT CTG AGT TTA TTG
 K   I   W   H   P   S   I   T   E   T   G   E   I   C   L   S   L   L 495  504       513       522       531       540
AGA GAA CAT TCA ATT GAT GGC ACT GGC TGG GCT CCC ACA AGA TTT CTT AAG GAT
 R   E   H   S   I   D   G   T   G   W   A   P   T   R   F   L   K   D 549  558       567       576       585       594
GTC GTT TGG GGA TTA AAC TCT TTG TTT ACT GAT CTT AAT TTT GAT AGT TTA CCA
 V   V   W   G   L   N   S   L   F   T   D   L   N   F   D   S   L   P 603  612       621       630       639       648
CTG AAT ATT GAA GCT GCA GAA CAT CAT TTG CGG GAC AAG GAG TTC CGG AAT
 L   N   I   E   A   A   E   H   H   L   R   D   K   E   F   R   N

FIGURE 1B
```

```
      657         666         675         684         693         702
AAA GTG GAT GAC TAC ATC AAA CGT TAT GCC AGA TGA AAG GGG ACG ATT GCA
 K   V   D   D   Y   I   K   R   Y   A   R
      711         720         729         738         747         756
GGC CCA ACT GTG TTA CAG TTT GTC TCT AAC ATG AAA CAG GAG GTA GCC
      765         774         783         792         801         810
CCC TCT CCC GTC CTC ATG CTC CCT CTC AGT CCC CTG GAT TGC CCC AGT CCT GTG
      819         828         837         846         855         864
ACC ATG TTG CCC TGA AGA AGA CCA TCT TCA TGA CTG CTC ATT GTA GAT GGA GAA
      873         882         891         900         909         918
TTC AAC ATA AAT ACA GCA AGA AAA TGT GTT TGG GCT TCT GAA GAG TTG TCT GCT
      927         936         945         954         963         972
TAC CTT AAC ATG TTT ACT TTT TTG AAC TTG TAC TGT TGT TGG TGA AAT
      981         990         999        1008        1017        1026
TCT TAA GAA GTT GTA ATG AAC TCA AAA TTG AGG CCA GAG CTT GCT TTC CCT TTT
     1035        1044        1053        1062        1071        1080
CCC AAA CAA AAT TGG TTT TCT GCA CAA GCG ATG CTA ATG ATG TCA GTG TAA
```

FIGURE 1C

```
     1089       1098       1107       1116       1125       1134
CTC GCA GAT TGG CAA TAA GAT ACC CGC TAC AAA CTG TGA TTG GAT GCA AAA TCT
     1143       1152       1161       1170       1179       1188
CTT AGC TTC TTT CAC GAA TGT TGG CCC TGC CTA GAT GTT GTG AAG CCT CCC AGA
     1197       1206       1215       1224       1233       1242
ATG CAT AGA GTC ATT CAC TGT AGA TCT CTT ATT GAA ATG CGT ATT TTA TTT AAT
     1251       1260       1269       1278       1287       1296
GTA AGT ATA TTT TGG AAC AGA TTT GTA ATT TGT ACA ATT CAA TGC TTT AAT TAT
     1305       1314       1323       1332       1341       1350
TTT TTC TAT TCT CAT TTA GTT TGT ATT TTC ATT GTA TAG AGC AGA CAG AAA GAT
     1359       1368       1377       1386       1395       1404
GTT GGG TCA AGC AAC TAT TGA AGA GAA ATA CAA AGA AAA TAT GAA AGG CAC ATT
     1413       1422       1431       1440       1449       1458
ATT CAT TTT GTC CAA ATG CAA TGA GAA TCT CAC TCT TAA AAA TCA GCT CTT GCT
     1467       1476       1485       1494       1503       1512
TTC GGG TCC GGA TGT GGT GAG CAC ATT TTG GAG CCC TTT GAA GCT AGA TTT GGA
```

FIGURE 1D

```
     1521            1530            1539            1548            1557       1566
TGA TCA AAA CAA AAA GGC AGG GAG CCC ATT CTA ACA TGC TGC CCA GAG GAA ACT 1575            1584            1593            1602            1611       1620
GGC TGG AGC CTG GAC CAG CTG GGG CTG ATG CTT TTG CAG TGG TCA TGT GAT TGT 1629            1638            1647            1656            1665       1674
GAC CTG GTA GCT ACT TAT CAG AGA GCC AGA CCC TGC TGT CCT GGG AGA CAG GAG 1683            1692            1701            1710            1719       1728
CGA TGC CTC AGG AAT CAG CCC AAT GTC TGA TGT CAC TGA GAC TGT ACC TGT GGC 1737            1746            1755            1764            1773       1782
CTT CTT CTG AGT TTG CTA TGG CTC CAG GCC CTG CCG GTG GGG TGA GCC TCC TAG 1791            1800            1809            1818            1827       1836
GCC TTG GAG GAC CAG GAG TCA ACA GTG GCA TAT GCC ATC CTC GGC CAG GTT AAT 1845            1854            1863            1872            1881       1890
ATA CTG CAG AGG AAA AGC CCT GAA GAG AGG CAA GTG GAT TTA CTC CAG CAT GTA 1899            1908            1917            1926            1935
GAC ATT TGA ACC AGT GAA ATC AAA CAC AAA ATA AAT ANC TGC TCT AGA A
```

FIGURE 1E

```
5' NNG CAG GAG GCA CGC GCG CGG CTG AGG CGA GGT CGC TCG GCG CAC TGT TGC GGG
                 9          18          27          36          45          54

GCC ATG GCG GGG ACC GCG CTC AAG AGG CTG ATG GCC GAG TAC AAA CAA TTA ACA
    A   M   A   G   T   A   L   K   R   L   M   A   E   Y   K   Q   L   T
                63          72          81          90          99         108

CTG AAT CCT CCG GAA ATT GTA GCA GGC CCC ATG AAT GAG AAC TTT TTT
    L   N   P   P   E   I   V   A   G   P   M   N   E   N   F   F
               117         126         135         144         153         162

GAA TGG GAG GCA TTG ATC ATG GGC CCA GAA GAC ACC TGC TTT GAG TTT GGT GTT
    E   W   E   A   L   I   M   G   P   E   D   T   C   F   E   F   G   V
               171         180         189         198         207         216

TTT CCT GCC ATC CTG AGT TTC CCA CTT GAT TAC CCG TTA AGT CCC CCA AAG ATG
    F   P   A   I   L   S   F   P   L   D   Y   P   L   S   P   P   K   M
               225         234         243         252         261         270

TTT CCT GAG ATG TTT CAT CCC AAC ATC TAC CCT GAT GGG AGA GTC ATG
    F   P   E   M   F   H   P   N   I   Y   P   D   G   R   V   M
               279         288         297         306         315         324

AGA TTT ACC TGT GAG ACC TGC
    R   F   T   C   E   T   C
```

FIGURE 2A

```
      333     342     351     360     369     378
ATT  TCC  ATC  CTC  CAC  GCG  CCA  GGC  GAT  GAC  CCC  ATG  GGC  TAC  GAG  AGC  AGC  GCG
 I    S    I    L    H    A    P    G    D    D    P    M    G    Y    E    S    S    A 387     396     405     414     423     432
GAG  CGG  TGG  AGT  CCT  GTG  CAG  AGT  GAA  GTG  GAG  AAG  ATC  CTG  CTG  TCG  GTG  AGC
 E    R    W    S    P    V    Q    S    E    V    E    K    I    L    L    S    V    S 441     450     459     468     477     486
ATG  CTG  GCA  GAG  CCC  AAT  GAC  GAA  AGT  GGA  GCT  AAC  GTG  GAT  GCG  TCC  AAA  ATG
 M    L    A    E    P    N    D    E    S    G    A    N    V    D    A    S    K    M 495     504     513     522     531     540
TGG  CGC  GAT  GAC  CGG  GAG  CAG  TTC  TAT  AAG  ATT  GCC  AAG  CAG  ATC  GTC  CAG  AAG
 W    R    D    D    R    E    Q    F    Y    K    I    A    K    Q    I    V    Q    K 549     558     567     576     585     594
TCT  CTG  GGA  CTG  TGA  GAC  CTG  GCC  TCG  CAC  ACA  CAC  CGC  ACC  GCC  AAT  CAG  CAG
 S    L    G    L 603     612     621     630     639     648
CTC  AGC  ATT  CTC  CCC  CGG  CAC  ACT  TAG  TGA  CAG  TGC  TCT  GTG  CTG  GTA  CCA
```

FIGURE 2B

```
 657              666              675              684              693              702
AAC AAG GCA   GAC TTG CAA   GAA CCA CGG   CAT CTT TTT   TTT TCA AAC   CTT TCC 711              720              729              738              747              756
AAA CAG GCT   TCT CTT CTG   AAA TGA TGA   CTT AAT GTC   GAA TAT TGA   CAG 765              774              783              792              801              810
GCA GTT TTA   CAG TAT TCC   TCA CAA AGG   GCT TCA GGT   AGA TTA TCA   GAG 819              828              837              846              855              864
GCA CTA CCT   CTC CCC GCT   GAA ACC AGC   AGT TCA TGG   CTT CCT GTG   GAT 873              882              891              900              909              918
CCT CCC TGG   AGT GTT GAG   GGG GTT GTA   CCT GCC AGA   CTT CCA GGG   GAC 927              936              945              954              963              972
ATA CCC AGA   ACG CTC CTT   CTG AAG AAA   TGG GGC CCT   GTA GCT GCA   GCA 981              990              999             1008             1017             1026
AAG GGC CCG   GCA CCC TTT   CTG GGT CCT   TCC TGG TTC   CCT GTG GGC   CCC 1035             1044             1053             1062             1071             1080
AGT CCA TTA   CTT TTC TTC   CTT CAT ATT   TTA CAG CAG   GCA GAT GCT   TTT
```

FIGURE 2C

```
            1089            1098           1107           1116           1125           1134
CTT ATA ATC TAA TTA CAT CTT TTC ATT TGT TAT ATA TTA CAA ACC ATC ACA CTT 1143           1152           1161           1170           1179           1188
AGA AAT ACT TCC AGG AAA TGC TTT TTT GAA GTG TGA ATT AAT AAG AAA TGG GGT 1197           1206
AAA TAG AAA AGA AAT TTA TTG CTG 3'
```

HUMAN UBIQUITIN-CONJUGATING ENZYMES

This application is a continuation-in-part application of co-pending U.S. patent application Ser. No. 08/933,750 entitled "Human Regulatory Molecules," filed Sep. 23, 1997, incorporated herein by reference in its entirety.

FIELD OF THE INVENTION

This invention relates to nucleic acid and amino acid sequences encoding human ubiquitin-conjugating enzymes and to the use of these sequences in the diagnosis, prevention, and treatment of neoplastic, immune, developmental, and neuronal disorders.

BACKGROUND OF THE INVENTION

The ubiquitin conjugation system (UCS) plays a major role in the degradation of cellular proteins in eukaroytic cells and in some bacteria. The UCS mediates the elimination of abnormal proteins and regulates the half-lives of other important regulatory proteins that control gene transcription and cell cycle progression. The UCS is reported to degrade mitotic cyclic kinases, oncoproteins, tumor suppressors, viral proteins, transcriptional regulators, and receptors associated with signal transduction (Verma, R. et al. (1997) Science 278:455–460; Ciechanover, A. (1994) Cell 79:13–21).

There are several steps in the process of ubiquitin conjugation and protein degradation (Jentsch, S. (1992) Annu. Rev. Genet. 26:179–207). First ubiquitin (Ub), a small, heat stable protein is activated by a ubiquitin-activating enzyme (E1). This activation involves an ATP dependent binding of the C-terminus of Ub to the thiol group of an internal cysteine residue of E1. Then activated Ub is transferred to one of several Ub-conjugating enzymes (E2). Each E2 has a recognition subunit which allows it to interact with proteins carrying a particular degradation signal. E2 links the Ub molecule through its C-terminal glycine to an internal lysine of the target protein. It must be noted that different ubiquitin-dependent proteolytic pathways employ structurally similar, but distinct, E2s, and in some instances, accessory factors known as ubiquitin-ligases or E3s, are required to work in conjunction with E2s for recognition of certain substrates. More than one Ub molecule may be needed to ubiquinate a target protein which subsequently is recognized and degraded by a proteasome. After degradation, Ub is released and reutilized.

Prior to activation, Ub is usually expressed as a fusion protein composed of an N-terminal ubiquitin and a C-terminal extension protein (CEP) or as a polyubiquitin protein with Ub monomers attached head to tail. CEPs bear similarities to a variety of regulatory proteins in that most are highly basic, contain up to 30% lysine and arginine residues, and have nucleic acid-binding domains (Monia, B. P. et al. (1989) J. Biol. Chem. 264:4093–4103). The fusion protein is an important intermediate form which appears to allow co-regulation of the cell's translational and protein degradation activities and to localize inactive enzyme to specific cellular sites. Once delivered, C-termninal hydrolases cleave the fusion protein releasing Ub to carry out its work (Monia et al., supra).

The E2s are important for substrate specificity in different UCS pathways. All E2s have a conserved UBC domain of approximately 16 kD and at least 35% identity and contain a centrally located cysteine residue which is required for ubiquitin-enzyme thiolester formation (Jentsch, supra). A highly conserved proline-rich element is located N-terminal to the active cysteine residue. Structural variations beyond the conserved domain are used to classify the E2 enzymes. The E2s of class 1 (E2-1) consist almost exclusively of the conserved UBC domain and include yeast E2-1 and UBCs 4, 5, and 7. These E2s are thought to require E3 to carry out their activities (Jentsch, supra). UBC7 has been shown to recognize ubiquitin as a substrate and to form polyubiquitin chains in vitro (Van Nocker, S. et al. (1996) J. Biol. Chem. 271:12150–58). E2s of class II (E2-2) have various unrelated C-terminal extensions that contribute to substrate specificity and cellular localization. The yeast E2-2 enzymes, UBC2 and UBC3, have highly acidic C-terminal extensions that promote interactions with basic substrates such as histones. Yeast UBC6 has a hydrophobic signal-anchor sequence that localizes the protein to the endoplasmic reticulum.

Defects or alterations in the normal activity of the UCS are associated with a number of diseases and disorders. These include increased ubiquitin-dependent proteolysis as associated with cachexia (Llovera M. et al. (1995) Int. J. Cancer 61:138–141), degradation of the tumor-suppressor protein, p53 (Ciechanover, supra), and neurodegeneration such as observed in Alzheimer's disease (Gregori L. et al. (1994) Biochem. Biophys. Res. Commun. 203:1731–1738). Since ubiquitin conjugation is a rate-limiting step in antigen presentation, the ubiquitin degradation pathway may also have a critical role in the immune response (Grant E. P. et al. (1995) J. Immunol. 155:3750–3758).

The discovery of new ubiquitin-conjugating enzymes and the polynucleotides encoding them satisfies a need in the art by providing new compositions useful in the diagnosis, prevention and treatment of neoplastic, immune, developmental, and neuronal disorders.

SUMMARY OF THE INVENTION

The invention features a substantially purified human vesicle trafficking protein (HUBI) comprising an amino acid sequence selected from the group consisting of SEQ ID NO:1 and SEQ ID NO:3.

The invention also provides a variant of human vesicle trafficking protein having at least 90% amino acid identity to the amino acid sequence of HUBI and which retains at least one functional characteristic of human HUBI.

The invention further provides an isolated and substantially purified polynucleotide sequence encoding a HUBI comprising the amino acid sequence of SEQ ID NO:1 or SEQ ID NO:3, and a composition comprising the polynucleotide sequence, or a fragment thereof. The invention also provides a polynucleotide sequence which hybridizes to the polynucleotide sequence encoding HUBI, or a fragment of the polynucleotide sequence. The invention further provides a polynucleotide sequence comprising the complement of the polynucleotide sequence encoding HUBI or a fragment or variant of the polynucleotide sequence.

The invention further provides an isolated and purified polynucleotide sequence selected from the group consisting of SEQ ID NO:2 and SEQ ID NO:4, or a fragment or a variant of the polynucleotide sequence. In addition, the invention provides a polynucleotide sequence which hybridizes to the polynucleotide sequence of SEQ ID NO:2 and SEQ ID NO:4. The invention also provides a polynucleotide sequence which is complementary to SEQ ID NO:2 and SEQ ID NO:4, or a fragment or a variant of the polynucleotide sequence.

The present invention further provides an expression vector containing at least a fragment of a polynucleotide sequence which encodes HUBI comprising the amino acid sequence of SEQ ID NO:1 or SEQ ID NO:3. In yet another aspect, the expression vector containing the polynucleotide sequence is contained within a host cell.

The invention also provides a method for producing HUBI, or a fragment of HUBI, the method comprising the steps of: a) culturing a host cell containing an expression vector containing at least a fragment of a polynucleotide sequence encoding HUBI under conditions suitable for the expression of the polypeptide; and b) recovering the polypeptide from the host cell culture.

The invention also provides a pharmaceutical composition comprising a substantially purified HUBI having the amino acid sequence of SEQ ID NO:1 or SEQ ID NO:3 in conjunction with a suitable pharmaceutical carrier.

The invention also provides a purified antagonist of HUBI. In one aspect, the invention provides a purified antibody which binds to HUBI.

Still further, the invention provides a purified agonist of HUBI.

The invention also provides a method for preventing or treating a neoplastic disorder comprising administering to a subject in need of such treatment an effective amount of an antagonist of HUBI.

The invention also provides a method for preventing or treating an immune disorder comprising administering to a subject in need of such treatment an effective amount of an antagonist of HUBI.

The invention also provides a method for preventing or treating an neuronal disorder comprising administering to a subject in need of such treatment an effective amount of an antagonist of HUBI.

The invention also provides a method for preventing or treating an developmental disorder comprising administering to a subject in need of such treatment an effective amount of an antagonist of HUBI.

The invention also provides a method for detecting a polynucleotide which encodes HUBI in a biological sample comprising the steps of: a) hybridizing the complement of the polynucleotide sequence which encodes HUBI to nucleic acid material of a biological sample, thereby forming a hybridization complex; and b) detecting the hybridization complex, wherein the presence of the complex correlates with the presence of a polynucleotide encoding HUBI in the biological sample. In one aspect, the nucleic acid material of the biological sample is amplified by the polymerase chain reaction prior to hybridization.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of human ubiquitin-conjugating enzyme, HUBI-1. The alignment was produced using MACDNASIS PRO software (Hitachi Software Engineering Co. Ltd. S. San Francisco, Calif.).

FIGS. 2A, 2B, 2C, and 2D show the amino acid sequence (SEQ ID NO:3) and nucleic acid sequence (SEQ ID NO:4) of human ubiquitin-conjugating enzyme, HUBI-2. The alignment was produced using MACDNASIS PRO software (Hitachi Software Engineering Co. Ltd. S. San Francisco, Calif.).

FIG. 3 shows the amino acid sequence alignments among HUBI-1 (1762; SEQ ID NO:1), C. elegans (GI 1628097; SEQ ID NO:5), HUBI-2 (2456290; SEQ ID NO:3), and S. cerevisiae (GI 4257; SEQ ID NO:6) produced using the multisequence alignment program of LASERGENE software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

HUBI, as used herein, refers to the amino acid sequences of substantially purified HUBI obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HUBI, increases or prolongs the duration of the effect of HUBI. Agonists may include proteins, nucleic acids, carbohydrates, or any other molecules which bind to and modulate the effect of HUBI.

An "allele" or "allelic sequence", as used herein, is an alternative form of the gene encoding HUBI. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HUBI, as used herein, include those with deletions, insertions, or substitutions of different nucleotides resulting in a polynucleotide that encodes the same or a functionally equivalent HUBI. Included within this definition are polymorphisms which may or may not be readily detectable using a particular oligonucleotide probe of the polynucleotide encoding HUBI, and improper or unexpected hybridization to alleles, with a locus other than the normal chromosomal locus for the polynucleotide sequence encoding HUBI. The encoded protein may also be "altered" and contain deletions, insertions, or substitutions of amino acid residues which produce a silent change and result in a functionally equivalent HUBI. Deliberate amino acid substitutions may be made on the basis of similarity in polarity, charge, solubility, hydrophobicity, hydrophilicity, and/or the amphipathic nature of the residues as long as the biological or immunological activity of HUBI is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of HUBI are preferably about 5 to about 15 amino acids in length and retain the biological activity or the immunological activity of HUBI. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer a Laboratory Manual*, Cold Spring Harbor Press, Plainview, N.Y.).

The term "antagonist", as used herein, refers to a molecule which, when bound to HUBI, decreases the amount or the duration of the effect of the biological or immunological activity of HUBI. Antagonists may include proteins, nucleic acids, carbohydrates, antibodies or any other molecules which decrease the effect of HUBI.

As used herein, the term "antibody" refers to intact molecules as well as fragments thereof, such as Fa, F(ab')$_2$, and Fv, which are capable of binding the epitopic determinant. Antibodies that bind HUBI polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HUBI, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding HUBI or fragments thereof may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using the XL-PCR Kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence .

The term "correlates with expression of a polynucleotide", as used herein, indicates that the detection of the presence of ribonucleic acid by northern analysis is indicative of the presence of mRNA encoding HUBI in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HUBI or the encoded HUBI. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear micro-chromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of HUBI. For example, modulation may cause an increase or a decrease in protein activity, binding characteristics, or any other biological, functional or immunological properties of HUBI.

"Nucleic acid sequence", as used herein. refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers","primers", "oligomers", and "probes", as commonly defined in the art.

"Peptide nucleic acid", PNA, as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence" which encompasses full-length HUBI and fragments thereof.

The term "sample", as used herein, is used in its broadest sense. A biological sample suspected of containing nucleic acid encoding HUBI, or fragments thereof, or HUBI itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HUBI, as used herein, refers to an amino acid sequence that is altered by one or more amino acids. The variant may have "conservative" changes, wherein a substituted amino acid has similar structural or chemical properties, e.g., replacement of leucine with isolcucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

THE INVENTION

The invention is based on the discovery of new human ubiquitin conjugating enzymes (hereinafter individually referred to as HUBI-1 and HUBI-2 and collectively, as HUBI ), the polynucleotides encoding HUBI, and the use of these compositions for the diagnosis, prevention, or treatment of neoplastic, immune, developmental, and neuronal disorders.

Nucleic acids encoding HUBI-1 of the present invention were first identified in Incyte Clone 1762 from the U937NOT01 cDNA library using a computer search for amino acid sequence alignments. A consensus sequence, SEQ ID NO:2, was derived from the extension and assembly of Incyte Clones 1762 (U937NOT01), 352606 (LVENNOT01), 1254927 (LUNGFET03), 1307911 (COLNFET02), 1359936 (LUNGNOT12), 1424618 (BEPINON01), 1503304 (BRAITUT07), 1833239 (BRAINON01), 2070865 (ISLTNOT01), and 2790509 (COLNTUT16).

In one embodiment, the invention encompasses a polypeptide comprising the amino acid sequence of SEQ ID NO:1, as shown in FIGS. 1A, 1B, 1C, 1D, and 1E. HUBI-1 is 185 amino acids in length and has a potential N-glycosylation site at $N_{108}$; seven potential phosphorylation sites at $T_{22}$, $S_{26}$, $T_{27}$, $S_{31}$, $T_{51}$, $T_{70}$, and $T_{35}$; a ubiquitin conjugation motif at $W_{105}$HPNITETGEICLSL; and a potential leucine zipper motif at $L_{136}$KDVVWGLNSLFTDL LNFDDPL. As shown in FIG. 3, HUBI-1 has chemical and structural homology with a Caenorhabditis elegans protein (GI 1628097). In particular, HUBI-1 and the C. elegans protein share 58% sequence identity, the phosphorylation sites at $T_{22}$, $T_{70}$, and $T_{135}$, the ubiquitin conjugation motif, the conserved $C_{116}$ and the leucine zipper motif. Northern analysis of HUBI-1 shows expression in various cDNA libraries, 47% of the which are associated with immune response, 35% of which are associated with neoplastic disorders, and 17% of which are associated with development.

Nucleic acids encoding HUBI-2 of the present invention were first identified in Incyte Clone 2456290 from the ENDANOT01 cDNA library using a computer search for amino acid sequence alignments. A consensus sequence, SEQ ID NO:4, was derived from the extension and assembly of Incyte Clones: 728911 (LUNGNOT03), 1515858 (PANCTUT01), 1602091 (BLADNOT03), 1808143 (SINTNOT13), 1918194 (PROSNOT06), 2025691 (KERANOT02), 2122672 (BRSTNOT07), 2180113 (SININOT01), 2456290 (ENDANOT01), and 3406014 (ESOGNOT03).

In one embodiment, the invention encompasses a polypeptide comprising the amino acid sequence of SEQ ID NO:3, as shown in FIGS. 2A, 2B, 2C, and 2D. HUBI-2 is 165 amino acids in length and has three potential phosphorylation sites at $T_{47}$, $S_{105}$, and $Y_{152}$ and a ubiquitin conjugation motif at $F_{78}$HPNIYPDGRVCISI. As shown in FIG. 3, HUBI-2 has chemical and structural homology with a Saccharomyces cerevisiae ubiquitin conjugating enzyme (GI 4257). In particular, HUBI-2 and the S. cerevisiae protein share 62% sequence identity, the phosphorylation sites at $T_{47}$ and $S_{105}$, the ubiquitin conjugation motif, and the conserved $C_{89}$. Northern analysis of HUBI-2 shows expression in various cDNA libraries; 31% of which are associated with cancers; 22% of the which are associated with immune response, and 16% of which are associated with the nervous system.

The invention also encompasses HUBI variants. A preferred HUBI variant is one having at least 80%, and more preferably at least 90%, amino acid sequence identity to the amino acid sequence claimed herein and which retains at least one biological, immunological or other functional characteristic or activity of HUBI. A most preferred HUBI variant is one having at least 95% amino acid sequence identity.

The invention also encompasses polynucleotides which encode HUBI. Accordingly, any nucleic acid sequence which encodes the amino acid sequence of HUBI can be used to produce recombinant molecules which express HUBI. In a particular embodiment, the invention encompasses the polynucleotides comprising the nucleic acid sequences of SEQ ID NO:2 and 4 as shown in FIGS. 1A–E and 2A–D, respectively.

It will be appreciated by those skilled in the art that as a result of the degeneracy of the genetic code, a multitude of nucleotide sequences encoding HUBI, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HUBI, and all such variations are to be considered as being specifically disclosed.

Although nucleotide sequences which encode HUBI and its variants are preferably capable of hybridizing to the nucleotide sequence of the naturally occurring HUBI under appropriately selected conditions of stringency, it may be advantageous to produce nucleotide sequences encoding HUBI or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HUBI and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HUBI and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HUBI or any fragment thereof.

Also encompassed by the invention are polynucleotide sequences that are capable of hybridizing to the claimed nucleotide sequences, and in particular, those shown in SEQ ID NOs:2 and 4, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio), Taq polymerase (PE Biosystems), thermostable T7 polymerase (Amersham Pharmacia Biotech, Piscataway, N.J.), or combinations of polymerases and proofreading exonucleases such as those found in the ELONGASE Amplification System marketed by Life Technologies (Gaithersburg, Md.). Preferably, the process is automated with machines such as the MICROLAB 2200 (Hamilton, Reno, Nev.), Peltier Thermal Cycler (PTC200; MJ Research, Watertown, Mass.) and the ABI Catalyst and 373 and 377 DNA Sequencers (PE BIOSYSTEMS).

The nucleic acid sequences encoding HUBI may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HUBI may be used in recombinant DNA molecules to direct expression of HUBI, fragments or functional equivalents thereof, in appropriate host cells. Due to the inherent degeneracy of the genetic code, other DNA sequences which encode substantially is the same or a functionally equivalent amino acid sequence may be produced, and these sequences may be used to clone and express HUBI.

As will be understood by those of skill in the art, it may be advantageous to produce HUBI-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HUBI encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HUBI may be ligated to a heterologous sequence to encode a fusion protein. For example, to screen peptide libraries for inhibitors of HUBI activity, it may be useful to encode a chimeric HUBI protein that can be recognized by a commercially available antibody. A fusion protein may also be engineered to contain a cleavage site located between the HUBI encoding sequence and the heterologous protein sequence, so that HUBI may be cleaved and purified away from the heterologous moiety.

In another embodiment, sequences encoding HUBI may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HUBI, or a fragment thereof. For example, peptide synthesis can be performed using various solid-phase techniques (Roberge, J. Y. et al. (1995) Science 269:202–204) and automated synthesis may be achieved, for example, using the ABI 431A Peptide synthesizer (PE Biosystems).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of HUBI, or any part thereof, may be altered during direct synthesis and/or combined using chemical methods with sequences from other proteins, or any part thereof, to produce a variant polypeptide.

In order to express a biologically active HUBI, the nucleotide sequences encoding HUBI or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HUBI and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding HUBI. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Life Technologies) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HUBI, vectors based on SV40 or EBV may be used with an appropriate selectable marker.

In bacterial systems, a number of expression vectors may be selected depending upon the use intended for HUBI. For example, when large quantities of HUBI are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding HUBI may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HUBI may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of *Science and Technology* (1992) McGraw Hill, New York, N.Y.; pp. 191–196).

An insect system may also be used to express HUBI. For example, in one such system, *Autographa californica* nuclear polyhedrosis virus (AcNPV) is used as a vector to express foreign genes in *Spodoptera frugiperda* cells or in Trichoplusia larvae. The sequences encoding HUBI may be cloned into a non-essential region of the virus, such as the polyhedrin gene, and placed under control of the polyhedrin promoter. Successful insertion of HUBI will render the polyhedrin gene inactive and produce recombinant virus lacking coat protein. The recombinant viruses may then be used to infect, for example, *S. frugiperda* cells or Trichoplusia larvae in which HUBI may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HUBI may be ligated into an adenovirus transcription/translation complex consisting of the late promoter and tripartite leader sequence. Insertion in a non-essential E1 or E3 region of the viral genome may be used to obtain a viable virus which is capable of expressing HUBI in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HUBI. Such signals include the ATG initiation codon and adjacent sequences. In cases where sequences encoding HUBI, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HUBI may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or aprt- cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HUBI is inserted within a marker gene sequence, transformed cells containing sequences encoding HUBI can be identified by the absence of marker gene function. Alternatively, a marker gene can be placed in tandem with a sequence encoding HUBI under the control of a single promoter. Expression of the marker gene in response to induction or selection usually indicates expression of the tandem gene as well.

Alternatively, host cells which contain the nucleic acid sequence encoding HUBI and express HUBI may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HUBI can be detected by DNA-DNA or DNA-RNA hybridization or amplification using probes or fragments or fragments of polynucleotides encoding HUBI. Nucleic acid amplification based assays involve the use of oligonucleotides or oligomers based on the sequences encoding HUBI to detect transformants containing DNA or RNA encoding HUBI.

A variety of protocols for detecting and measuring the expression of HUBI, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HUBI is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HUBI include oligolabeling, nick translation, end-labeling or PCR amplification using a labeled nucleotide. Alternatively, the sequences encoding HUBI, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP. and labeled nucleotides. These procedures may be conducted using a variety of commercially available kits (Amersham Pharmacia Biotech, Promega, and US Biochemical). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HUBI may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HUBI may be designed to contain signal sequences which direct secretion of HUBI through a prokaryotic or eukaryotic cell membrane. Other constructions may be used to join sequences encoding HUBI to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HUBI may be used to facilitate purification. One such expression vector provides for expression of a fusion protein containing HUBI and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992) Prot. Exp. Purif. 3:263–281) while the enterokinase cleavage site provides a means for purifying HUBI from the fusion protein. A discussion of vectors which contain fusion proteins is provided in Kroll, D. J. et al. (1993; DNA Cell Biol. 12:441–453).

In addition to recombinant production, fragments of HUBI may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using ABI 431A Peptide synthesizer (PE Biosystems). Various fragments of HUBI may be chemically synthesized separately and combined using chemical methods to produce the full length molecule.

Therpaeutics

Chemical and structural homology exists among HUBI and the protein sequences of C. elegans (GI 1628097) and S. cerevisiae (GI 4257). In addition, HUBI is expressed in neoplastic, immune, developmental, and neuronal disorders where HUBI plays a role in the cell cycle and in cell signaling.

Degradation of tumor suppressor proteins such as p53 by E2 enzymes may contribute to the development of neoplastic disorders. Therefore, in one embodiment, an antagonist of HUBI may be administered to a subject to prevent or treat a neoplastic disorder. Such disorders may include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HUBI may be used directly as an antagonist or indirectly as a targeting or delivery mechanism for bringing a pharmaceutical agent to cells or tissue which express HUBI.

Abnormalities in processing of neural proteins (AP) by enzymes of the UCS may contribute to neuronal disorders. Since HUBI appears to be involved in UCS dependent proteolysis and is found in neuronal tissues, an antagonist of HUBI may be administered to a subject to prevent or treat a neuronal disorder. Such disorders may include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, Parkinson's disease, paranoid psychoses, schizophrenia, and Tourette's disorder.

In another embodiment, an antagonist of HUBI may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma.

In another embodiment, an antagonist of HUBI may be administered to a subject to prevent or treat a developmental disorder. Such disorders include, but are not limited to, renal tubular acidosis, Cushing's syndrome, achondroplastic dwarfism, Duchenne and Becker muscular dystrophy, gonadal dysgenesis, myelodysplastic syndrome, hereditary mucoepithelial dysplasia, hereditary keratodermas, hereditary neuropathies such as Charcot- Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss.

In another embodiment, a vector expressing the complement of the polynucleotide encoding HUBI may be administered to a subject to treat or prevent neoplastic disorder including, but not limited to, the types of cancer described above.

In another embodiment, a vector expressing the complement of the polynucleotide encoding HUBI may be administered to a subject to treat or prevent a neuronal disorder including, but not limited to, those described above.

In another embodiment, a vector expressing the complement of the polynucleotide encoding HUBI may be administered to a subject to treat or prevent an immune disorder including, but not limited to, those described above.

In another embodiment, a vector expressing the complement of the polynucleotide encoding HUBI may be administered to a subject to treat or prevent developmental disorder including, but not limited to, the those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HUBI may be produced using methods which are generally known in the art. In particular, purified HUBI may be used to produce antibodies or to screen libraries of pharmaceutical agents to identify those which specifically bind HUBI.

Antibodies to HUBI may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HUBI or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HUBI have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HUBI amino acids may be fused with those of another protein such as keyhole limpet hemocyanin and antibody produced against the chimeric molecule.

Monoclonal antibodies to HUBI may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HUBI-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for HUBI may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HUBI and its specific antibody. A two-site, monoclonal-based immunoassay utilizing monoclonal antibodies reactive to two non-interfering HUBI epitopes is preferred, but a competitive binding assay may also be employed (Maddox, supra).

In another embodiment of the invention, the polynucleotides encoding HUBI, or any fragment or complement thereof, may be used for therapeutic purposes. In one aspect, the complement of the polynucleotide encoding HUBI may be used in situations in which it would be desirable to block the transcription of the mRNA. In particular, cells may be transformed with sequences complementary to polynucleotides encoding HUBI. Thus, complementary molecules or fragments may be used to modulate HUBI activity, or to achieve regulation of gene function. Such technology is now well known in the art, and sense or antisense oligonucleotides or larger fragments, can be designed from various locations along the coding or control regions of sequences encoding HUBI.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HUBI. These techniques are described both in Sambrook et al. (supra) and in Ausubel et al. (supra).

Genes encoding HUBI can be turned off by transforming a cell or tissue with expression vectors which express high levels of a polynucleotide or fragment thereof which encodes HUBI. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing to complementary sequences or antisense molecules (DNA, RNA, or PNA) to the control, 5' or regulatory regions of the gene encoding HUBI (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HUBI.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HUBI. Such DNA sequences may be incorporated into a wide variety of vectors with suitable RNA polymerase promoters such as T7 or SP. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HUBI, antibodies to HUBI, mimetics, agonists, antagonists, or inhibitors of HUBI. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HUBI, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HUBI or fragments thereof, antibodies of HUBI, agonists, antagonists or inhibitors of HUBI, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therpeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HUBI may be used for the diagnosis of conditions or diseases characterized by expression of HUBI, or in assays to monitor patients being treated with HUBI, agonists, antagonists or inhibitors. The antibodies useful for diagnostic purposes may be prepared in the same manner as those described above for therapeutics. Diagnostic assays for HUBI include methods which utilize the antibody and a label to detect HUBI in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HUBI are known in the art and provide a basis for diagnosing altered or abnormal levels of HUBI expression. Normal or standard values for HUBI expression are established by combining body fluids or cell extracts taken from normal mammalian subjects, preferably human, with antibody to HUBI under conditions suitable for binding The amount of binding may be quantified by various methods, but preferably by photometric means. Quantities of HUBI expressed in subject, control, and disease, samples from biopsied tissues are compared with the standard values. Deviation between standard and subject values establishes the parameters for diagnosing disease.

In another embodiment of the invention, the polynucleotides encoding HUBI may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HUBI may be correlated with disease. The diagnostic assay may be used to distinguish between absence, presence, and excess expression of HUBI, and to monitor regulation of HUBI levels during therapeutic intervention.

In one aspect, hybridization with PCR probes which are capable of detecting polynucleotide sequences, including genomic sequences, encoding HUBI or closely related molecules, may be used to identify nucleic acid sequences which encode HUBI. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HUBI, alleles, or related sequences.

Probes may also be used for the detection of related sequences, and should preferably contain at least 50% of the nucleotides encoding HUBI. The hybridization probes of the subject invention may be DNA or RNA and derived from the nucleotide sequences of SEQ ID NOs:2 and 4 or from genomic sequences which include promoter, enhancer elements, and introns of the naturally occurring HUBI.

Means for producing specific hybridization probes for DNAs encoding HUBI include the cloning of nucleic acid sequences encoding HUBI or HUBI derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HUBI may be used for the diagnosis of conditions or disorders which are associated with expression of HUBI. Examples of such conditions or disorders include neoplastic disorders such as adenocarcinoma, leukemia, lymphoma, melanoma, myeloma, sarcoma, teratocarcinoma and cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; neuronal disorders such as akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, Parkinson's disease, paranoid psychoses, schizophrenia, and Tourette's disorder; immune disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; and developmental disorders such as renal tubular acidosis, Cushing's syndrome, achondroplastic dwarfism, Duchenne and Becker muscular dystrophy, gonadal dysgenesis, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss. The polynucleotide sequences encoding HUBI may be used in Southern or northern analysis, dot blot, or other membrane-based technologies; in PCR technologies; or in dipstick, pin, ELISA assays or microarrays utilizing fluids or tissues from patient biopsies to detect altered HUBI expression. Such qualitative or quantitative methods are well known in the art.

In a particular aspect, the nucleotide sequences encoding HUBI may be useful in assays that detect activation or induction of various cancers, particularly those mentioned above. The nucleotide sequences encoding HUBI may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HUBI in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HUBI, a normal or standard profile for expression is established. This may be accomplished by combining body fluids or cell extracts taken from normal subjects, either animal or human, with a sequence, or a fragment thereof, which encodes HUBI, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HUBI may involve the use of PCR. Such oligomers may be chemically synthesized, generated enzymatically, or produced in vitro. Oligomers will preferably consist of two nucleotide sequences, one with sense orientation (5'->3') and another with antisense (3'->5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HUBI include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, understanding the genetic basis of disease, diagnosing disease, and in developing and in monitoring the activities of therapeutic agents.

In further embodiments, oligonucleotides or longer fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, understanding the genetic basis of disease, diagnosing disease, and in developing and in monitoring the activities of therapeutic agents.

In one embodiment, the microarray is prepared and used according to the methods described in PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619), all of which are incorportated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell or tissue type or to a normal, developmental, or disease state. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from 2 to one million.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon or other type of membrane, filter, chip, glass slide, or any other suitable solid support.

In another aspect, the oligonucleotides may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot or slot blot HYBRIDOT apparatus (Life Technologies) may be used to arrange and link cDNA fragments or oligonucleotides to the surface of a substrate using a vacuum system, thermal, UV, mechanical or chemical bonding procedures. In yet another aspect, an array may be produced by hand or using available devices, materials, and machines (including multichannel pipettors or robotic instruments; Brinkmann, Westbury, N.Y.) and may contain 8, 24, 96, 384 1536 or 6144 oligonucleotides, or any other multiple from 2 to one million which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, complementary nucleic acid sequences are used as probes and can also include polynucleotides, fragments, complementary, or antisense sequences produced using restriction enzymes, PCR technologies, and oligolabeling kits (Amersham Pharmacia Biotech) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. A detection system may be used to measure the absence, presence, and amount of hybridization for all of the distinct sequences simultaneously. This data may be used for large scale correlation studies or functional analysis of the sequences, mutations, variants, or polymorphisms among samples (Heller, R. A. et al., (1997) Proc. Natl. Acad. Sci. 94:2150–55).

In another embodiment of the invention, the nucleic acid sequences which encode HUBI may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding HUBI on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HUBI, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HUBI and the agent being tested, may be measured.

Another technique for drug screening which may be used provides for high throughput screening of compounds having suitable binding affinity to the protein of interest as described in published PCT application WO84/03564. In this method, as applied to HUBI large numbers of different small test compounds are synthesized on a solid substrate, such as plastic pins or some other surface. The test compounds are reacted with HUBI, or fragments thereof, and washed. Bound HUBI is then detected by methods well known in the art. Purified HUBI can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HUBI specifically compete with a test compound for binding HUBI. In this manner, the antibodies can be used to detect the presence of any peptide which shares one or more antigenic determinants with HUBI.

In additional embodiments, the nucleotide sequences which encode HUBI may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

U937NOT01

The U937 cDNA library, U937NOT01, was constructed by Stratagene (STR937207), using RNA isolated from the U937 monocyte-like cell line. This cell line (ATCC CRL1593) was established by C. Sundstrom and K. Nilsson in 1974 (Int. J. Cancer 17:565–577) from malignant cells obtained from the pleural effusion of a 37-year-old Caucasian male with diffuse histiocytic lymphoma. cDNA synthesis was initiated using an XhoI-oligo d(T) primer. Double-stranded cDNA was blunted, ligated to EcoRI adaptors, digested with XhoI, size-selected, and cloned into the XhoI and EcoRI sites of the Lambda UniZAP vector (Stratagene). The vector was transformed into *E. coli* host strain XL1-BLUE (Stratagene) The cDNA library was screened with DNA probes and the phagemids were obtained by the in vivo excision process, in which the host bacterial strain was coinfected with both the lambda library phage and an f1 helper phage. Polypeptides derived from both the library-containing phage and the helper phage nicked the lambda DNA, initiated new DNA synthesis from defined sequences on the lambda target DNA and created a smaller, single stranded circular phagemid DNA molecule that included all DNA sequences of the PBLUESCRIPT plasmid and the cDNA insert. The phagemid DNA was secreted from the cells, purified, and used to transform fresh host cells where double-stranded phagemid DNA was produced. The newly-transfected bacteria were selected on medium containing ampicillin.

ENDANOT01

The ENDANOT01 cDNA library was constructed from an aortic endothelial cell line derived from explanted heart/aorta tissue obtained from a male (specimen #A062).

The frozen cells were homogenized and lysed using a Brinkmann Homogenizer Polytron PT-3000 (Brinkmann Instruments, Westbury, N.Y.) in guanidinium isothiocyanate solution. The lysate was centrifuged over a 5.7 M CsCl cushion using a Beckman SW28 rotor in a Beckman L8-70M Ultracentrifuge (Beckman, Fullerton, Calif.) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNAse at 37° C. The RNA extraction and precipitation were repeated two times as before. The mRNA was isolated with the OLIGOTEX kit and used to construct the cDNA library.

The mRNA was handled according to the recommended protocols in the SuperScript Plasmid System for cDNA Synthesis and Plasmid Cloning (Cat. #18248–013; Life Technologies). The cDNAs were fractionated on a SEPHAROSE CL4B column (Cat. #275105–01; Amersham Pharmacia Biotech), and those cDNAs exceeding 400 bp were ligated into pINCY 1. (Incyte Pharmaceuticals, Palo Alto, Calif. The plasmid pINCY 1 was subsequently transformed into DH5α competent cells (Cat. #18258–012; Life Technologies).

II Isolation and Sequencing of cDNA Clones

U937NOT01

Phagemid DNA was purified using the MAGIC MINI-PREPS DNA purification system (Catalogue #A7100, Promega Corp., Madison, Wis.). The DNA was eluted from the purification resin already prepared for DNA sequencing and other analytical manipulations. Alternatively, phagemid DNA may be purified using the QIAWELL8, QIAWELL PLUS and QIAWELL ULTRA DNA purification systems (QIAGEN Inc., Chatsworth, Calif.).

The cDNA inserts from random isolates of the U-937 library were sequenced in part. Methods for DNA sequencing are well known in the art. Conventional enzymatic methods employ DNA polymerase Kienow fragment, SEQUENASE or Taq polymerase to extend DNA chains from an oligonucleotide primer annealed to the DNA template of interest. Methods have been developed for the use of both single and double stranded templates. The chain termination reaction products were electrophoresed on urea-acrylamide gels and were detected either by autoradiography (for radionuclide-labeled precursors) or by fluorescence (for fluorescent-labeled precursors).

ENDANOT10

Plasmid DNA was released from the cells and purified using the REAL Prep 96 plasmid kit (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul SF (1993) J Mol Evol 36:290–300; Altschul, SF et al (1990) J Mol Biol 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith, R. F. and T. F. Smith (1992; Protein Engineering 5:35–51), incorporated herein by reference, can be used when dealing with primary sequence patterns and secondary structure gap penalties. As disclosed in this application, sequences have lengths of at least 49 nucleotides and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searches matches between a query sequence and a database sequence, to evaluate the statistical significance of any matches found, and to report only those matches which satisfy the user-selected threshold of significance. In this application, threshold is set at 10–25 for nucleotides and 10–14 for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J.Mol.Evol. 36:290–300; Altschul, S. F. et al. (1990) J.Mol.Evol. 215:403–410) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \text{maximum BLAST score} \ 100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HUBI occurs. Abundance and percent abundance are also reported. Abundance directly reflects the number of times a particular transcript is represented in a cDNA library, and percent abundance is abundance divided by the total number of sequences examined in the cDNA library.

V Extension of HUBI Encoding Polynucleotides

The nucleic acid sequences of the Incyte Clone 1762 and 2456290 were used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68' to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (PE Biosystems) and thoroughly mixing the enzyme and reaction mix. Beginning with 40 pmol of each primer and the recommended concentrations of all other components of the kit, PCR was performed using the DNAENGINE thermal cycler (PTC200; M.J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NOs:2 and 4 are used to obtain 5' regulatory sequences using the procedure above, oligonucleotides designed for 5' extension, and an appropriate genomic library.

VI Labeling and Use of Individual Hybridization Probes

Hybridization probes derived from SEQ ID NOs:2 and 4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi of [$\gamma$-$^{32}$p] adenosine triphosphate (Amersham Pharmacia Biotech) and T4 polynucleotide kinase (DuPont NEN, Boston, Mass.). The labeled oligonucleotides are substantially purified with SEPHADEX G-25 superfine resin column (Amersham Pharmacia Biotech). A aliquot containing $10^7$ counts per minute of the labeled probe is used in a typical membrane-based hybridization analysis of human genomic DNA digested with one of the following endonucleases (Ase I, Bgl II, Eco RI, Pst 1, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Eastman Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, SEQ ID NO:2 and SEQ ID NO:4 are examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized in the presence of fluorescent or radioactive nucleotides and arranged on the surface of the substrate. When the substrate is a silicon chip, a light-directed chemical process is used for deposition (Chee, M. et al., PCT/WO95/11995, incorporated herein by reference).

In the alternative, a chemical coupling procedure and an ink jet device is used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray is washed to remove nonhybridized probes, and a detection device as simple as X-ray film or complicated as a light scanner is used to determine the levels and patterns of radioactivity or fluorescence. Scanned fluorescent images are examined to determine degree of complementarity and the relative abundance/expression level of each oligonucleotide sequence in the microarray.

VIII Complementary Polynucleotides

Sequence complementary to the HUBI-encoding sequence, or any part thereof, is used to decrease or inhibit expression of naturally occurring HUBI. Although use of oligonucleotides comprising from about 15 to about 30 base-pairs is described, essentially the same procedure is used with smaller or larger sequence fragments. Appropriate oligonucleotides are designed using OLIGO 4.06 software and the coding sequence of HUBI. To inhibit transcription, a complementary oligonucleotide is designed from the most unique 5' sequence and used to prevent promoter binding to the coding sequence. To inhibit translation, a complementary oligonucleotide is designed to prevent ribosomal binding to the transcript encoding HUBI.

IX Expression of HUBI

Expression of HUBI is accomplished by subcloning the cDNAs into appropriate vectors and transforming the vectors into host cells. In this case, the cloning vector is also used to express HUBI in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HUBI into the bacterial growth media which can be used directly in the following assay for activity.

X Demonstration of HUBI Activity

HUBI activity is demonstrated by the formation of di-ubiquitin conjugates from free ubiquitin (van Nocker et al. supra). HUBI is incubated together with 75 pmol $^{125}$I-labeled ubiquitin, 20 nM wheat E1, 2 mM Mg ATP, 0.1 mM dithiothreitol, and 50 mM Tris-HCl, pH 8.0. The reaction is incubated for 2 minutes at 4° C. and the di-ubiquitin product separated from free ubiquitin by polyacrylamide gel electrophoresis. Di-ubiquitin is visualized by autoradiography, removed from the gel, and counted in a gamma radioisotope counter. The amount of di-ubiquitin formed in the reaction is proportional to the activity of HUBI in the assay.

XI Production of HUBI Specific Antibodies

HUBI that is substantially purified using PAGE electrophoresis (Sambrook, supra), or other purification techniques, is used to immunize rabbits and to produce antibodies using standard protocols. The amino acid sequences deduced from SEQ ID NO:2 and SEQ ID NO:4 are analyzed using LASERGENE software (DNASTAR Inc) to determine regions of high immunogenicity and corresponding oligopeptides are synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an ABI Peptide Synthesizer 431A(PE Biosystem) using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HUBI Using Specific Antibodies

Naturally occurring or recombinant HUBI is substantially purified by immunoaffinity chromatography using antibodies specific for HUBI. An immunoaffinity column is constructed by covalently coupling HUBI antibody to an activated chromatographic resin, such as CNBr-activated SEPHAROSE (Amersham Parmacia Biotech). After the coupling, the resin is blocked and washed according to the manufacturer's instructions.

Media containing HUBI is passed over the immunoaffinity column, and the column is washed under conditions that allow the preferential absorbance of HUBI (e.g., high ionic strength buffers in the presence of detergent). The column is eluted under conditions that disrupt antibody/HUBI binding (eg, a buffer of pH 2–3 or a high concentration of a chaotrope, such as urea or thiocyanate ion), and HUBI is collected.

XIII Identification of Molecules Which Interact with HUBI

HUBI or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled HUBI, washed and any wells with labeled HUBI complex are assayed. Data obtained using different concentrations of HUBI are used to calculate values for the number, affinity, and association of HUBI with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. An isolated and purified composition comprising the polynucleotide sequence of claim 1.

3. A polynucleotide sequence which is fully complementary to the polynucleotide sequence of claim 1.

4. An isolated and purified polynucleotide sequence consisting of SEQ ID NO:2.

5. A composition comprising the polynucleotide sequence of claim 4.

6. An isolated and purified polynucleotide sequence which is fully complementary to the polynucleotide sequence of claim 4.

7. An expression vector containing the polynucleotide sequence of claim 1.

8. A host cell containing the expression vector of claim 7.

9. A method for producing the polypeptide having the amino acid sequence of SEQ ID NO:1, the method comprising the steps of:

a) culturing the host cell of claim 8 under conditions suitable for the expression of the polypeptide; and b) recovering the polypeptide from the host cell culture.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 185 amino acids
       (B) TYPE: amino acid
       (C) STRANDEDNESS: single
       (D) TOPOLOGY: linear (vii) IMMEDIATE SOURCE:
       (A) LIBRARY: U937NOT01
       (B) CLONE: 1762

(xi) SEQUENCE DESCRIPTION: SEQ ID NO:1:

Met Leu Thr Leu Ala Ser Lys Leu Lys Arg Asp Asp Gly Leu Lys Gly
 1               5                  10                  15

Ser Arg Thr Ala Ala Thr Ala Ser Asp Ser Thr Arg Arg Val Ser Val
                20                  25                  30

Arg Asp Lys Leu Leu Val Lys Glu Val Ala Glu Leu Glu Ala Asn Leu
            35                  40                  45

Pro Cys Thr Cys Lys Val His Phe Pro Asp Pro Asn Lys Leu His Cys
50                  55                  60

Phe Gln Leu Thr Val Thr Pro Asp Glu Gly Tyr Tyr Gln Gly Gly Lys
65                  70                  75                  80

Phe Gln Phe Glu Thr Glu Val Pro Asp Ala Tyr Asn Met Val Pro Pro
                85                  90                  95

Lys Val Lys Cys Leu Thr Lys Ile Trp His Pro Asn Ile Thr Glu Thr
               100                 105                 110

Gly Glu Ile Cys Leu Ser Leu Leu Arg Glu His Ser Ile Asp Gly Thr
           115                 120                 125

Gly Trp Ala Pro Thr Arg Thr Leu Lys Asp Val Val Trp Gly Leu Asn
       130                 135                 140

Ser Leu Phe Thr Asp Leu Leu Asn Phe Asp Asp Pro Leu Asn Ile Glu
145                 150                 155                 160

Ala Ala Glu His His Leu Arg Asp Lys Glu Asp Phe Arg Asn Lys Val
                165                 170                 175

Asp Asp Tyr Ile Lys Arg Tyr Ala Arg
                180                 185

(2) INFORMATION FOR SEQ ID NO:2:

(i) SEQUENCE CHARACTERISTICS:
       (A) LENGTH: 1937 base pairs
       (B) TYPE: nucleic acid
       (C) STRANDEDNESS: single
       (D) TOPOLOGY: linear (vii) IMMEDIATE SOURCE:
       (A) LIBRARY: U937NOT01
       (B) CLONE: 1762

(xi) SEQUENCE DESCRIPTION: SEQ ID NO:2:

```
CGCCGCCGGG AGCCGGTGCG GCTGTGAGGG GCCGCGTCTC GCAGCAGCCG CCCGGACCGG    60

GCATGGTGTT GGGCGCCGGG CCCGCCTCGC CTGTCTCGGG GAGCCCAGGG TAAAGGCAGC   120

AGTAATGCTA ACGCTAGCAA GTAAACTGAA GCGTGACGAT GGTCTCAAAG GGTCCCGGAC   180

GGCAGCCACA GCGTCCGACT CGACTCGGAG GGTTTCTGTG AGAGACAAAT TGCTTGTTAA   240
```

```
AGAGGTTGCA GAACTTGAAG CTAATTTACC TTGTACATGT AAAGTGCATT TTCCTGATCC    300

AAACAAGCTT CATTGTTTTC AGCTAACAGT AACCCCAGAT GAGGGTTACT ACCAGGGTGG    360

AAAATTTCAG TTTGAAACTG AAGTTCCCGA TGCGTACAAC ATGGTGCCTC CCAAAGTGAA    420

ATGCCTGACC AAGATCTGGC ACCCCAACAT CACAGAGACA GGGGAAATAT GTCTGAGTTT    480

ATTGAGAGAA CATTCAATTG ATGGCACTGG CTGGGCTCCC ACAAGAACAT TAAAGGATGT    540

CGTTTGGGGA TTAAACTCTT TGTTTACTGA TCTTTTGAAT TTTGATGATC CACTGAATAT    600

TGAAGCTGCA GAACATCATT TGCGGGACAA GGAGGACTTC CGGAATAAAG TGGATGACTA    660

CATCAAACGT TATGCCAGAT GATAAAGGG GACGATTGCA GGCCCATGGA CTGTGTTACA     720

GTTTGTCTCT AACATGAAAC AGCAAGAGGT AGCCCCCTCT CCCGTCCTCA TGCTCCCTCT    780

CAGTCCCCTG GATTGCCCCA GTCCTGTGAC CATGTTGCCC TGAAGAAGAC CATCTTCATG    840

ACTGCTCATT GTAGATGGAG AATTCAACAT AAATACAGCA AGAAAATGTG TTTGGGCTTC    900

TGAAGAGTTG TCTGCTTACC TTAACATGTT TACTTTTTTG AACTTGTACT GTATAGGCTG    960

TTGGTGAAAT TCTTAAGAAG TTGTAATGAA CTCAAAATTG AGGCCAGAGC TTGCTTTCCC   1020

TTTTCCCAAA CAAAATTGGT TTTCTGCACA AGCGATGCTA ATGATGTGTT CAGTGTAACT   1080

CGCAGATTGG CAATAAGATA CCCGCTACAA ACTGTGATTG GATGCAAAAT CTCTTAGCTT   1140

CTTTCACGAA TGTTGGCCCT GCCTAGATGT TGTGAAGCCT CCCAGAATGC ATAGAGTCAT   1200

TCACTGTAGA TCTCTTATTG AAATGCGTAT TTTATTTAAT GTAAGTATAT TTTGGAACAG   1260

ATTTGTAATT TGTACAATTC AATGCTTTAA TTATTTTTTC TATTCTCATT TAGTTTGTAT   1320

TTTCATTGTA TAGAGCAGAC AGAAAGATGT TGGGTCAAGC AACTATTGAA GAGAAATACA   1380

AAGAAAATAT GAAAGGCACA TTATTCATTT TGTCCAAATG CAATGAGAAT CTCACTCTTA   1440

AAAATCAGCT CTTGCTTTCG GGTCCGGATG TGGTGAGCAC ATTTTGGAGC CCTTTGAAGC   1500

TAGATTTGGA TGATCAAAAC AAAAAGGCAG GGAGCCCATT CTAACATGCT GCCCAGAGGA   1560

AACTGGCTGG AGCCTGGACC AGCTGGGGCT GATGCTTTTG CAGTGGTCAT GTGATTGTGA   1620

CCTGGTAGCT ACTTATCAGA GAGCCAGACC CTGCTGTCCT GGGAGACAGG AGCGATGCCT   1680

CAGGAATCAG CCCAATGTCT GATGTCACTG AGACTGTACC TGTGGCCTTC TTCTGAGTTT   1740

GCTATGGCTC CAGGCCCTGC CGGTGGGGTG AGCCTCCTAG GCCTTGGAGG ACCAGGAGTC   1800

AACAGTGGCA TATGCCATCC TCGGCCAGGT TAATATACTG CAGAGGAAAA GCCCTGAAGA   1860

GAGGCAAGTG GATTTACTCC AGCATGTAGA CATTTGAACC AGTGAAATCA AACACAAAAT   1920

AAATANCTGC TCTAGAA                                                   1937
```

(2) INFORMATION FOR SEQ ID NO:3:

(i) SEQUENCE CHARACTERISTICS:
        (A) LENGTH: 165 amino acids
        (B) TYPE: amino acid
        (C) STRANDEDNESS: single
        (D) TOPOLOGY: linear (vii) IMMEDIATE SOURCE:
        (A) LIBRARY: ENDANOT01
        (B) CLONE: 2456290

(xi) SEQUENCE DESCRIPTION: SEQ ID NO:3:

```
Met Ala Gly Thr Ala Leu Lys Arg Leu Met Ala Glu Tyr Lys Gln Leu
 1               5                  10                  15

Thr Leu Asn Pro Pro Glu Gly Ile Val Ala Gly Pro Met Asn Glu Glu
            20                  25                  30
```

```
Asn Phe Phe Glu Trp Glu Ala Leu Ile Met Gly Pro Glu Asp Thr Cys
         35                  40                  45

Phe Glu Phe Gly Val Phe Pro Ala Ile Leu Ser Phe Pro Leu Asp Tyr
 50                  55                  60

Pro Leu Ser Pro Pro Lys Met Arg Phe Thr Cys Glu Met Phe His Pro
 65                  70                  75                  80

Asn Ile Tyr Pro Asp Gly Arg Val Cys Ile Ser Ile Leu His Ala Pro
                 85                  90                  95

Gly Asp Pro Met Gly Tyr Glu Ser Ser Ala Glu Arg Trp Ser Pro
                100                 105                 110

Val Gln Ser Val Glu Lys Ile Leu Leu Ser Val Val Ser Met Leu Ala
            115                 120                 125

Glu Pro Asn Asp Glu Ser Gly Ala Asn Val Asp Ala Ser Lys Met Trp
130                 135                 140

Arg Asp Asp Arg Glu Gln Phe Tyr Lys Ile Ala Lys Gln Ile Val Gln
145                 150                 155                 160

Lys Ser Leu Gly Leu
                165

(2) INFORMATION FOR SEQ ID NO:4:

(i) SEQUENCE CHARACTERISTICS:
        (A) LENGTH: 1210 base pairs
        (B) TYPE: nucleic acid
        (C) STRANDEDNESS: single
        (D) TOPOLOGY: linear (vii) IMMEDIATE SOURCE:
        (A) LIBRARY: ENDANOT01
        (B) CLONE: 2456290

(xi) SEQUENCE DESCRIPTION: SEQ ID NO:4:

GCAGGAGGCA CGCGCGCGGC TGAGGCGAGG TCGCTCGGCG CACTGTTGCG GGGCCATGGC     60

GGGGACCGCG CTCAAGAGGC TGATGGCCGA GTACAAACAA TTAACACTGA ATCCTCCGGA    120

AGGAATTGTA GCAGGCCCCA TGAATGAAGA GAACTTTTTT GAATGGGAGG CATTGATCAT    180

GGGCCCAGAA GACACCTGCT TTGAGTTTGG TGTTTTTCCT GCCATCCTGA GTTTCCCACT    240

TGATTACCCG TTAAGTCCCC CAAAGATGAG ATTTACCTGT GAGATGTTTC ATCCCAACAT    300

CTACCCTGAT GGGAGAGTCT GCATTTCCAT CCTCCACGCG CCAGGCGATG ACCCCATGGG    360

CTACGAGAGC AGCGCGGAGC GGTGGAGTCC TGTGCAGAGT GTGGAGAAGA TCCTGCTGTC    420

GGTGGTGAGC ATGCTGGCAG AGCCCAATGA CGAAAGTGGA GCTAACGTGG ATGCGTCCAA    480

AATGTGGCGC GATGACCGGG AGCAGTTCTA TAAGATTGCC AAGCAGATCG TCCAGAAGTC    540

TCTGGGACTG TGAGACCTGG CCTCGCACAG GCGCACACAC ACCGCCAATC AGCTCAGCAT    600

TCTCCCCCGG CACACTTAGT GACAGTGATG CTCTGTGCTG GTACCAAACA AGGCAGACTT    660

GCAAGAACCA CGGCATCTTT TTTTTTTTTC AAACCTTTCC TACTTCAAAC AGGCTTCTCT    720

TCTGAAATGA TGACTTAATG TCGAATATTG ACAGCTTACT GCAGTTTTAC AGTATTCCTC    780

ACAAAGGGCT TCAGGTAGAT TATCAGAGCT GTCAGCACTA CCTCTCCCCG CTGAAACCAG    840

CAGTTCATGG CTTCCTGTGG ATTCCCTCCC TCCTGGAGT GTTGAGGGGG TTGTACCTGC    900

CAGACTTCCA GGGGACGATG GAATACCCAG AACGCTCCTT CTGAAGAAAT GGGGCCCTGT    960

AGCTGCAGCA CAGGGGAAGG GCCCGGCACC CTTTCTGGGT CCTTCCTGGT TCCCTGTGGG   1020

CCCCATGAGG AGTCCATTAC TTCCTTTCTT CCTTCATATT TTACAGGCAG ATGCTTTTCT   1080

TATAATCTAA TTACATCTTT TCATTTGTTA TATATTACAA ACCATCACAC TTAGAAATAC   1140
```

```
TTCCAGGAAA TGCTTTTTTG AAGTGTGAAT TAATAAGAAA TGGGGTAAAT AGAAAAGAAA    1200

TTTATTGCTG                                                          1210
```

(2) INFORMATION FOR SEQ ID NO:5:

(i) SEQUENCE CHARACTERISTICS:
        (A) LENGTH: 180 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1628097

(xi) SEQUENCE DESCRIPTION: SEQ ID NO:5:

```
Met Phe Asn Leu Gln Lys Arg Ile Asn Gly Asn Glu Asp Gly Arg
 1               5                  10                  15

Tyr Leu Glu Thr Arg Ile Ala Val Arg Asp Lys Leu Leu Ala Gln Glu
                20                  25                  30

Leu Gln Gln Leu Glu Thr Ala Leu Arg Asp Gln Lys Gln Lys Leu Trp
            35                  40                  45

His Leu Glu Val Pro Ser Thr Ser Cys Leu His Glu Leu Glu Leu Thr
    50                  55                  60

Val Thr Pro Gln Glu Gly Ile Tyr Arg Gly Gly Lys Phe Arg Phe Lys
65                  70                  75                  80

Ile Thr Val Pro Pro Glu Tyr Asn Asn Val Pro Val Val Lys Cys
                85                  90                  95

Leu Thr Lys Val Trp His Pro Asn Ile Asn Glu Asp Gly Ser Ile Cys
            100                 105                 110

Leu Ser Ile Leu Arg Gln Asn Ser Leu Asp Gln Tyr Gly Trp Arg Pro
        115                 120                 125

Thr Arg Asn Leu Thr Asp Val Val His Gly Leu Val Ser Leu Phe Asn
    130                 135                 140

Asp Leu Met Asp Phe Asn Asp Ala Leu Asn Ile Gln Ala Ala Gln Met
145                 150                 155                 160

Trp Ser Gln Asn Arg Glu Ser Phe Asn His Arg Val Arg Glu Tyr Ile
                165                 170                 175

Ser Arg Tyr Cys
            180
```

(2) INFORMATION FOR SEQ ID NO:6:

(i) SEQUENCE CHARACTERISTICS:
        (A) LENGTH: 165 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 4257

(xi) SEQUENCE DESCRIPTION: SEQ ID NO:6:

```
Met Ser Lys Thr Ala Gln Lys Arg Leu Leu Lys Glu Leu Gln Gln Leu
 1               5                  10                  15

Ile Lys Asp Ser Pro Pro Gly Ile Val Ala Gly Pro Lys Ser Glu Asn
                20                  25                  30

Asn Ile Phe Ile Trp Asp Cys Leu Ile Gln Gly Pro Pro Asp Thr Pro
            35                  40                  45

Tyr Ala Asp Gly Val Phe Asn Ala Lys Leu Glu Phe Pro Lys Asp Tyr
```

-continued

```
            50                      55                      60
Pro Leu Ser Pro Pro Lys Leu Thr Phe Thr Pro Ser Ile Leu His Pro
65                  70                  75                  80

Asn Ile Tyr Pro Asn Gly Glu Val Cys Ile Ser Ile Leu His Ser Pro
                85                  90                  95

Gly Asp Asp Pro Asn Met Tyr Glu Leu Ala Glu Glu Arg Trp Ser Pro
            100                 105                 110

Val Gln Ser Val Glu Lys Ile Leu Leu Ser Val Met Ser Met Leu Ser
        115                 120                 125

Glu Pro Asn Ile Glu Ser Gly Ala Asn Ile Asp Ala Cys Ile Leu Trp
    130                 135                 140

Arg Asp Asn Arg Pro Glu Phe Glu Arg Gln Val Lys Leu Ser Ile Leu
145                 150                 155                 160

Lys Ser Leu Gly Phe
                165
```